United States Patent [19]

Pert

[11] Patent Number: 5,567,682
[45] Date of Patent: Oct. 22, 1996

[54] METHOD OF TREATING ALZHEIMER'S DISEASE

[75] Inventor: Candace B. Pert, Potomac, Md.

[73] Assignee: Advanced Peptides and Biotechnology Sciences, Sewickely, Pa.

[21] Appl. No.: 346,334

[22] Filed: Nov. 29, 1994

Related U.S. Application Data

[63] Continuation of Ser. No. 44,903, Apr. 6, 1993, abandoned, which is a continuation of Ser. No. 831,088, Feb. 7, 1992, abandoned, which is a continuation of Ser. No. 551,048, Jul. 11, 1990, abandoned, which is a continuation of Ser. No. 285,074, Dec. 16, 1988, abandoned.

[51] Int. Cl.$^6$ ............................ A61K 38/07; A61K 38/08
[52] U.S. Cl. ................................ 514/15; 514/16; 514/17; 514/18
[58] Field of Search ........................... 514/16, 17, 15, 514/18; 530/328, 329, 330

[56] References Cited

U.S. PATENT DOCUMENTS

| | | | |
|---|---|---|---|
| 4,613,500 | 9/1986 | Suzuki et al. | 429/85 |
| 4,985,242 | 1/1991 | Sekine et al. | 424/85.4 |
| 5,063,206 | 11/1991 | Bridge et al. | 514/16 |

FOREIGN PATENT DOCUMENTS

| | | | |
|---|---|---|---|
| 0249390 | 12/1987 | European Pat. Off. | 514/16 |
| 0249394 | 12/1987 | European Pat. Off. | 514/16 |
| 579363 | 1/1994 | European Pat. Off. | |
| 07614 | 12/1987 | WIPO . | |

OTHER PUBLICATIONS

Pert, C. B., et al., Psychopharmacology Bull., 24(3): 315–319, 1988.
Pert, C. B., et al. Ann. Neurol., 23 (Suppl.): S71–S73, 1988.
Pert, C. B., et al., Proc. Natl. Acad. Sci., USA, 83: 9254–9258, Dec. 1986.
Cecil Textbook of Medicine 19th ed. pp. 2076–2077 (1992).
Rosen et al, American Journal on Addictions vol. 1 p. 332 (1992).

*Primary Examiner*—Jeffrey E. Russel
*Attorney, Agent, or Firm*—McAulay Fisher Nissen Goldberg & Kiel

[57] ABSTRACT

The present invention relates to a method of treating the symptoms of Alzheimer's disease by the intranasal administration of a therapeutically effective amount of specific short chain peptides, in particular peptide T, to patients. Intranasal administration of the defined short chain peptides promotes neuronal survival for reducing or halting the progressive neuronal degeneration which occurs in Alzheimer's disease.

8 Claims, No Drawings

METHOD OF TREATING ALZHEIMER'S DISEASE

This application is a continuation of application Ser. No. 08/044,903 filed Apr. 6, 1993 abandoned, which was a continuation of application Ser. No. 07/831,088 filed Feb. 7, 1992, abandoned, which was a continuation of application Ser. No. 07/551,048 filed Jul. 11, 1990, abandoned, which was a continuation of application Ser. No. 07/285,074, filed Dec. 16, 1988, abandoned.

This invention relates to the prophylaxis and/or treatment of Alzheimer's disease, a form of dementia of unknown etiology.

BACKGROUND OF THE INVENTION

Dementia is a syndrome of progressive, irreversible cerebral dysfunction caused by structural neropathologic alterations and characterized by cognitive functional loss. The condition is characterized by a slow disintegration of personality and intellect due to impaired insight and judgement. Alzheimer-type dementia is due to a degenerative process, the most prominent early symptom being memory loss. Alzheimer3 s presenile dementia typically begins in the fifties and sixties; senile onset dementia begins in the seventies and eighties. The dementia usually progresses steadily, becoming well advanced in two or three years.

Vasoactive intestinal peptide, or VIP, is reported to cause various biological actions in humans and animals. This peptide has actions on the cardiovascular system, where it promotes vasodilation of various vessels, on the respiratory system, and on the endocrine system. In the central nervous system, it provokes an excitation of cerebral-cortical and spinal cord neurons, hyperthermia, and stimulation of glucose utilization. The five-amino-acid (TDNYT) sequence of positions 7–11 of VIP shares homology with the pentapeptide TTNYT of Peptide T (described in more detail below) which interferes with the proposed attachment sequence of the human immunodeficiency virus (HIV). The HIV envelope glycoprotein, gp120, is responsible for viral binding to the T4 molecule. Peptide T inhibits gp120 binding to human T cells and inhibits human T cell infectivity. This suggests the possibility that VIP, or certain fragments of it, are endogenous ligands for the T4 receptor as reported by Sacerdote, Ruff and Pert, *Journal of Neuroscience Research*, 18:102–107 (1987).

Alzheimer's disease or dementia is believed to be caused by deterioration of the cholinergic neurons in the basal forebrain. Vasoactive intestinal polypeptide is co-localized with cholinergic neurons in most parts of the body, including the cholinergic neurons in the basal forebrain. Vasoactive intestinal polypeptide tends to maintain neuronal survival. In a proposed secondary phase of Alzheimer's disease, endogenous neurons of the cortex of various different chemical types degenerate following deprivation of their vasoactive intestinal polypeptide neuronal growth factor which was once contained in the cholinergic endings.

DESCRIPTION OF THE INVENTION

Described is a method of treating Alzheimer's disease in which a person suffering from Alzheimer's dementia is administered a therapeutically effective amount of a peptide of the formula:

$$R^a\text{-Ser-Thr-Thr-Thr-Asn-Tyr-}R^b \quad \text{(I)}$$

where $R^a$ represents an amino terminal residue Ala- or D-Ala- and $R^b$ represents a carboxy terminal residue -Thr or -Thr amide or a derivative thereof, with an additional Cys- residue at one or both of the amino and carboxy terminals, or a peptide of the formula:

$$R^1\text{-}R^2\text{-}R^3\text{-}R^4\text{-}R^5 \quad \text{(II)}$$

where $R^1$ is an amino terminal residue Thr-, Ser-, Asn-, Leu-, Ile-, Arg- or Glu-; $R^2$ is Thr, Ser or Asp; $R^3$ is Thr, Ser, Asn, Arg, Gln Lys or Trp; $R^4$ is Tyr and $R^5$ is a carboxy terminal amino group or a derivative thereof with a corresponding D-amino acid as the amino terminal residue, and/or a corresponding amide derivative at the carboxy terminal residue and/or additionally a Cys- residue at one or both of the amino and carboxy terminals or the physiologically acceptable salts thereof. Also the peptide may have the formula $X\text{-}R^1\text{-}R^2\text{-}R^3\text{-}R^4\text{-}R^5\text{-}X$, where $R^1\text{-}R^5$ are as defined above and X is cysteine. Preferred peptides are ala-ser-thr-thr-thr-asn-tyr-thr, thr-thr-asn-tyr-thr, ser-ser-thr-tyr-arg, asn-thr-ser-tyr-thr, thr-thr-ser-tyr-thr, ser-ser-thr-tyr-arg, asn-thr-ser-tyr-gly, ser-thr-asn-tyr-arg, ser-ser-thr-tyr-arg, ser-ser-arg-tyr-arg, ser-ser-thr-tyr-arg, thr-thr-ser-tyr-ser, and cys-thr-thr-asn-tyr-thr-cys. The peptide is preferably conjugated to a protein, such as human serum albumin. Preferably, the peptide is ASTTTNYT, also known as Peptide T.

The peptide is administered in a therapeutically effective amount, that is an amount sufficient to diminish or stop the patient's loss of cerebral function. Usually, the amount administered is an amount of from 0.2 to 10 mg, preferably 0.5 to 5 mg, per day for a 70 kg adult human. The peptide is administered parenterally or, preferably, intranasally.

Also disclosed is a method of arresting the degeneration and loss of cerebral function in a person having Alzheimer's disease comprising administering to that person a therapeutically effective amount of a peptide of the formula:

$$R^a\text{-Ser-Thr-Thr-Thr-Asn-Tyr-}R^b \quad \text{(I)}$$

where $R^a$ represents an amino terminal residue Ala- or D-Ala- and $R^b$ represents a carboxy terminal residue -Thr or -Thr amide or a derivative thereof, with an additional Cys- residue at one or both of the amino and carboxy terminals, or a peptide of the formula:

$$R^1 R^2\text{-}R^3\text{-}R^4\text{-}R^5 \quad \text{(II)}$$

where $R^1$ is an amino terminal residue Thr-, Ser-, Asn-, Leu-, Ile-, Arg- or Glu-; $R^2$ is Thr, Ser or Asp; $R^3$ is Thr, Set, Asn, Arg, Gln, Lys or Trp; $R^4$ is Tyr and $R^5$ is a carboxy terminal amino group or a derivative thereof with a corresponding D-amino acid as the amino terminal residue, and/or a corresponding amide derivative at the carboxy terminal residue and/or additionally a Cys- residue at one or both of the amino and carboxy terminals, or the physiologically acceptable salts thereof, and continuing the administration on a maintenance basis to prevent or,diminish further degeneration of cerebral function. Preferably, the peptide is administered in an amount such that deterioration of the cholinergic neurons in the basal forebrain is at least reduced or, preferably, stabilized.

While not wishing to be bound to any particular theory or mode:of operation, the short chain peptides described herein, notably Peptide T, act on T4 receptors, to promote neuronal survival, which is believed to prevent the progressive cellular degeneration which occurs in Alzheimer's disease and may prove useful in the treatment/stabilization of other diseases and conditions benefiting from procedures that promote neuronal survival.

The use of peptides as herein described are believed to be of most therapeutic benefit as a prophylactic when given early in the degenerative course of the disease to prevent further deterioration. Such therapeutic intervention addresses the basic etiology of the disease, so far as it is known, i.e., the disappearance of various neurons in the cortex. Like HIV-induced dementia, Alzheimer's disease is a true dementia characterized by the loss of neurons.

It is clinically established that peptidergic neurons disappear in the cortex as Alzheimer's disease progresses, following initial loss and degeneration of the basal forebrain nucleus. VIP/peptide T is believed to be a growth factor for these neurons, hence effective in at least arresting the otherwise inevitable degeneration of the basal forebrain nucleus and the patient's condition.

The peptides used in the therapeutic procedures of this invention are known materials and are described as relatively small or short peptides of up to 30 amino acids having the general formula:

$$R^a\text{-Ser-Thr-Thr-Thr-Asn-Tyr-}R^b \qquad (I)$$

where $R^a$ represents an amino terminal residue Ala- or D-Ala- and $R^b$ represents a carboxy terminal residue -Thr or -Thr amide, or a derivative thereof with an additional Cys-residue at one or both of the amino and carboxy terminals, or a peptide of the formula:

$$R^1\text{-}R^2\text{-}R^3\text{-}R^4\text{-}R^5 \qquad (II)$$

where $R^1$ is an amino terminal residue Thr-, Ser-, Asn-, Leu-, Ile-, Arg- or Glu-; $R^2$ is Thr, Ser or Asp; $R^3$ is Thr, Ser, Asn, Arg, Gln, Lys or Trp; $R^4$ is Tyr and $R^5$ is a carboxy terminal amino group or a derivative thereof with a corresponding D-amino acid as the amino terminal residue, and/or a corresponding amide derivative at the carboxy terminal residue and/or additionally a Cys- residue at one or both of the amino and carboxy terminals. Physiologically acceptable saltis of these peptides are also included. Also the peptide may have the formula $X\text{-}R^1\text{-}R^2\text{-}R^3\text{-}R^4\text{-}R^5\text{-}X$ where $R^1\text{-}R^5$ are as defined above and X is cysteine. Preferred peptides are ala-ser-thr-thr-thr-asn-tyr-thr, thr-thr-asn-tyr-thr, ser-ser-thy-tyr-arg, asn-thr-ser-tyr-thr, thr-thr-ser-tyr-thr, ser-ser-thr-tyr-arg, asn-thr-ser-tyr-gly, ser-thr-asn-tyr-arg, ser-ser-thr-tyr-arg, ser-ser-arg-tyr-arg, ser-ser-thr-tyr-arg, thr-thr-ser-tyr-ser, and cys-thr-thr-asn-tyr-thr-cys. The peptide is preferably conjugated to a protein, such as human serum albumin.

The preferred peptide is the octapeptide ASTTTNYT also known as Peptide T.

These peptides bind to the T4 receptors and are useful in preventing viral infectability, notably retroviruses, Which bind to the T4 receptors and act as competitive blocking agents. These peptides are currently under study in the treatment of HIV infections, and are described in PCT application PCT/US87/01345 published as WO 87/07614 on Dec. 17, 1987 in the names of Pert, Ruff and Farrar, the disclosure of which is hereby incorporated by reference to the extent necessary to facilitate the understanding of this application.

Amounts of the short peptide is administered in therapeutically effective amounts, that is they are administered in amounts and/or at dosage intervals sufficient to provide threrapeutic benefit to the Alzheimer's patient. Typically, the amounts administered are generally within the range of about 0.2 mg to 10 mg, preferably 0.5 to 5 mg, per day calculated on the weight of a 70 kg adult human. The peptide may be administered in divided doses and is administered parenterally, usually by injection or infusion.

A preferred route of administration is intranasally either as a dry (lyopholized) neat powder or as an aqueous solution, preferably a sterile, isotonic solution. The peptide is dissolved in physiologicsaline in concentrations of from 0.01 to 50 mg/ml, preferably 1 to 50 mg/ml.

What is claimed is:

1. A method of treating the symptoms of Alzheimer's disease by reducing or halting a loss of neurons, comprising intranasally administering to a person suffering from Alzheimer's dementia a therapeutically effective amount of a peptide of the formula:

$$R^a\text{-Ser-Thr-Thr-Thr-Asn-Tyr-}R^b \qquad (I)$$

where $R^a$ represents an amino terminal residue Ala- or D-Ala- and $R^b$ represents a carboxyl terminal residue -Thr or Thr amide and/or an additional Cys-residue at one or both of the amino and carboxyl terminals, or a peptide of the formula:

$$R^1\text{-}R^2\text{-}R^3\text{-}R^4\text{-}R^5 \qquad (II)$$

where $R^1$ is an amino terminal residue Thr-, Ser-, Asn-, Leu-, Ile-, Arg- or Glu-; $R^2$ is Thr, Ser or Asp; $R^3$ is Thr, Ser, Asn, Arg, Gln, Lys or Trp; $R^4$ is Tyr; and $R^5$ is a carboxyl terminal amino group with a corresponding D-amino acid as the amino terminal residue, and/or a corresponding amide derivative at the carboxyl terminal residue and/or additionally a Cys-residue at one or both of the amino and carboxyl terminals, or a physiologically acceptable salt thereof.

2. The method of claim 1, in which the peptide is ASTTTNYT.

3. The method of claim 1 or 2, in which the peptide is administered in an amount of from about 0.2 to about 10 mg per day for a 70 kg adult human.

4. The method of claim 3, in which the amount of peptide administered is from 0.5 to 5 mg per day.

5. A method of treating the symptoms of Alzheimer's disease by arresting neuronal degeneration and loss in a person having Alzheimer's disease comprising intranasally administering to that person a therapeutically effective amount of a peptide of the formula:

$$R^a\text{-Ser-Thr-Thr-Thr-Asn-Tyr-}R^b \qquad (I)$$

where $R^a$ represents an amino terminal residue Ala- or D-Ala- and $R^b$ represents a carboxyl terminal residue -Thr or Thr amide and/or an additional Cys-residue at one or both of the amino and carboxyl terminals, or a peptide of the formula:

$$R^1\text{-}R^2\text{-}R^3\text{-}R^4\text{-}R^5 \qquad (II)$$

where $R^1$ is an amino terminal residue Thr-, Ser- Asn-, Leu-, Ile-, Arg- or Glu-; $R^2$ is Thr, Ser or Asp; $R^3$ is Thr, Ser, Asn, Arg, Gln, Lys or Trp; $R^4$ is Tyr; and $R^5$ is a carboxyl terminal amino group with a corresponding D-amino acid as the amino terminal residue, and/or a corresponding amide derivative at the carboxyl terminal residue and/or additionally a Cys-residue at one or both of the amino and carboxyl terminals, or a physiologically acceptable salt thereof, and continuing said intranasal administration to prevent or diminish further neuronal degeneration.

6. The method of claim 5, in which the peptide is ASTTTNYT.

7. The method of claim 5, or 9 in which the peptide is administered in an amount of from 0.2 to 10 mg per day for a 70 kg adult human.

8. The method of claim 5, in which the amount of peptide administered is from 0.5 to 5 mg per day.

* * * * *